(12) United States Patent
McNeff et al.

(10) Patent No.: US 7,544,376 B2
(45) Date of Patent: Jun. 9, 2009

(54) METHODS AND COMPOSITIONS FOR INCREASING MILK PRODUCTION IN ANIMALS

(75) Inventors: Larry C. McNeff, Anoka, MN (US); Clayton V. McNeff, Andover, MN (US)

(73) Assignee: SarTec Corporation, Anoka, MN (US)

( * ) Notice: Subject to any disclaimer, the term of this patent is extended or adjusted under 35 U.S.C. 154(b) by 0 days.

(21) Appl. No.: 11/193,032

(22) Filed: Jul. 29, 2005

(65) Prior Publication Data

US 2006/0024387 A1    Feb. 2, 2006

Related U.S. Application Data

(60) Provisional application No. 60/592,801, filed on Jul. 30, 2004.

(51) Int. Cl.
   *A61K 36/48*     (2006.01)
   *A61K 36/82*     (2006.01)
   *A61K 36/00*     (2006.01)

(52) U.S. Cl. .................. 424/757; 424/725; 424/729; 424/773

(58) Field of Classification Search .................. None
   See application file for complete search history.

(56) References Cited

U.S. PATENT DOCUMENTS

| | | | |
|---|---|---|---|
| 4,388,327 | A | 6/1983 | Cummins |
| 5,139,779 | A | 8/1992 | McNeff |
| 5,219,596 | A | 6/1993 | Smith et al. |
| 5,496,571 | A | 3/1996 | Blagdon et al. |
| 7,138,125 | B2 * | 11/2006 | Emery et al. .............. 424/234.1 |

FOREIGN PATENT DOCUMENTS

| | | |
|---|---|---|
| EP | 1088483 A1 * | 4/2001 |
| WO | WO 03056935 A1 * | 7/2003 |

OTHER PUBLICATIONS

Lila, Z.A.; Mohammed, N.; Kanda, S.; Kamada, T.; Itabashi, H. J. Dairy Sci. 2003; 86: 3330-3336.*
http://web.archive.org/web/19981202101633/http://www.foodsci.uoguelph.ca/dairyedu/biosynthesis.html. (Web Publication Date: Dec. 2, 1998). Date Accessed: May 15, 2006.*
Murphy, K.D.; Johnson, D.G.; Appleman, R.D.; Otterby, D.E. J. Dairy Sci. 1991; 74: 2708-2717.*
Wilson, R.C.; Overton, T.R.; Clark, J.H. J. Dairy Sci. 1998; 81: 1022-1027.*
http://www.extenza-eps.com/AOAC/doi/abs/10.5555/jaoi.2000.83.6.1451;jsessionid=o58x_ptaAnThIdpNjT?cookieSet=1&journalCode=jaoi (Date Accessed: May 15, 2006).*
http://www.ag.ndsu.edu/pubs/ansci/beef/coping/underfed.htm.*
http://web.archive.org/web/*/http://www.cals.ncsu.edu/an_sci/extension/animal/meatgoat/MGFrgnds.htm. (Web Publication Date: Oct. 17, 2000). Date Accessed: Jul. 23, 2007.*
http://web.archive.org/web/20030620083858/http://www.kellymom.com/bf/supply/milkproduction.htm. (Web Publication Date:Jun. 20, 2003). Date Accessed: Jul. 23, 2007.*
http://web.archive.org/web/*/http://www.pregnancy.org/article.php?sid=1044. (Web Publication Date: Jan. 27, 2004). Date Accessed: Jul. 23, 2007.*
Grant R.J and Keown J. F. 'Feeding Dairy Cattle for Proper Body Condition Scoring'. Copyright 1999, University of Missouri. Published by University Extension, University of Missouri-Columbia.*
Cheeke, P. R., "Actual and potential applications *Yucca schidigera* and *Quillaja saponaria* saponins in human and animal nutrition", *Proc. Am. Soc. Anim. Sci., 1999* (www.asas.org/symposia/proceedings/0909.pdf), (2000).
Dehority, Burk A., "Evaluation of Subsampling and Fixation Procedures Used for Counting Rumen Protozoa", *Appl. Environ. Microbiol. 48(1)*, (Jul. 1984),182-185.
Dumitru, Razvan , "Targeting Methanopterin Biosynthesis To Inhibit Methanogenesis", *Appl. Environ. Microbiol. 69(12)*, (Dec. 2003),7236-7241.
Fahmy, Wael G., "Effect of Defaunation and Amino Acid Supplementation on Growth and Amino Acid Balance in Sheep", (Aug. 5, 1998).
Francis, George , "The biological action of saponins in animal systems: a review.", *Br. J. Nutr. 88(6)*, (2002),587-605.
Garcia-Lopez, P. M., "In Vitro Inhibition of Microbial Methane Production by 9,10-Anthraquinone", *J. Anim. Sci. 74*, (1996),2276-2284.
Goodall, S. R., "Rumensin with and without Sarsaponin for Finishing Feedlot Steers", *Col. Agr. Exp. Station No. 700*, (1981).
Goodall, S. R., "Sarsaponin effects upon ruminal VFA concentrations and weight gain of feedlot cattle", *J. Anim. Sci. 49*, (1979),377-382.
Goodall, Richard S., "Sarsaponin in Beef Cattle Rations", *Beef Nutrition Research*, (1978),9-10.
Goodall, S. R., "The Effect of Sarsaponin with and without Rumensin in High-Energy Diets", *Col. Agr. Exp. Station No. 700*, (1981).
Hristov, Alexander N., "Effect of *Yucca schidigera* on ruminal fermentation and nutrient digestion in heifers", *J. Anim Sci. 77*, (1999),2554-2563.
Klita, P. T., "Effects of alfalfa root saponins on digestive function in sheep", *J. Animal Sci. 74*, (1996),1144-1156.
Koenig, K. M., "Effects of protozoa on bacterial nitrogen recycling in the rumen", *J. Anim Sci. 78*, (2000),2431-2445.
Lila, Z. A., "Effect of Sarsaponin on Ruminal Fermentation with Particular Reference to Methane Production in Vitro", *J. Dairy Sci. 86*, (2003),3330-3336.
Lu, C. D., "Alfalfa saponins affect site and extent of nutrient digestion in ruminants", *J. Nutr. 117*, (1987),919-927.

(Continued)

*Primary Examiner*—Christopher R. Tate
(74) *Attorney, Agent, or Firm*—Pauly, DeVries Smith & Deffner, L.L.C.

(57) ABSTRACT

The invention is related to methods and compositions for increasing milk production in animals using a saponin containing composition. In an embodiment, the invention is a method for increasing milk production of an animal comprising administering an initiation dose of a saponin-containing composition to the animal within five days before or after the time of freshening of the animal, and administering a plurality of maintenance doses of the saponin-containing composition to the animal.

8 Claims, 3 Drawing Sheets

OTHER PUBLICATIONS

Mendoza, G. D., "Influence of ruminal protozoa on site and extent of starch digestion and ruminal fermentation", *J. Anim Sci. 71.* (1993),1572-1578.

Miller, Terry L., et al., "Inhibition of Growth of Methane-Producing Bacteria of the Ruminant Forestomach by Hydroxymethylglutaryl-SCoA Reductase Inhibitors", *J. Dairy Sci. 84(6)*, (Jun. 2001),1445-1448.

Navas-Camacho, Alberto, "Effect of reducing the rumen ciliate protozoa population by feeding saponin-containing plants on rumen function of sheep fed on wheat straw", *Arch. Latinoam. Prod. Anim. 5(Supp. 1)*, (1997),98-101.

Rush, Ivan, "Grain Tempering Agent (SarTemp) for Corn in Finishing Rations", *Beef Cattle Report*, (1993),63-64.

Towne, Gene, "Omasal Ciliated Protozoa in Cattle, Bison, and Sheep", *Appl. Environ. Microbiol. 56(2)*, (Feb. 1990),409-412.

Valdez, F. R., "Effect of Steroidal Sapogenins on Ruminal Fermentation and on Production of Lactating Dairy Cows", *J. Dairy Sci. 69*, (1986),1568-1575.

Wallace, R. J., "Influence of *Yucca shidigera* Extract on Ruminal Ammonia Concentrations and Ruminal Microorganisms", *Appl. Environ. Microbiol. 60(6)*, (Jun. 1994),1762-1767.

Wang, Y., "Effects of *Yucca schidigera* extract on fermentation and degradation of steroidal sponins in the rumen simulation technique (RUSITEC)", *Animal Feed Sci. Technol. 74*, (1998),143-153.

Wilson, R. C., "Effects of *Yucca shidigera* Extract and Soluble Protein on Performance of Cows and Concentrations of Urea Nitrogen in Plasma and Milk", *J. Dairy Sci. 81*, (1998),1022-1027.

Zinn, R. A., "Influence of tempering on the feeding value of rolled corn in finishing diets for feedlot cattle", *J. Anim Sci. 76*, (1998),2239-2246.

Wattiaux, Michel A., et al., "Chapter 1: Digestion in the Dairy Cow", *The Babcock Institute for International Dairy Research and Development-The University of Wisconsin Madison*, http://babcock.wisc.edu/downloads/de_html/ch01.en.html, 6 pages, Mar. 5, 2003.

\* cited by examiner

METHODS AND COMPOSITIONS FOR INCREASING MILK PRODUCTION IN ANIMALS

CROSS REFERENCE TO RELATED APPLICATION

This application claims the benefit of U.S. Provisional Patent Application Ser. No. 60/592,801, filed Jul. 30, 2004, which application is hereby incorporated by reference in its entirety.

FIELD OF THE INVENTION

The invention is related to methods and compositions for increasing milk production in animals. More specifically, the invention is related to methods and compositions for increasing milk production in animals using a saponin containing composition.

BACKGROUND OF THE INVENTION

Increasing the milk production of lactating dairy cattle is an ongoing challenge facing the dairy industry. The digestive system of the dairy cow is one aspect to consider in facing this challenge. Ingested feed first passes into the reticulorumen, where it is subject to anaerobic microbial fermentation. This microbial fermentation begins the digestive process and gives the ruminant the ability to utilize fibrous feeds that the mammalian system alone cannot break down due to the lack of necessary enzyme systems. The host animal subsequently meets her own nutrient needs by utilizing the by-products of this extensive fermentation, along with any undigested feed residues and the resultant microbial mass that passes from the rumen.

Different techniques have been utilized in order to boost milk production including hormonal modulation and feed additives. Examples of feed additive techniques can be found in U.S. Pat. No. 5,496,571 (Blagdon et al.), U.S. Pat. No. 5,219,596 (Smith et al.), and U.S. Pat. No. 4,388,327 (Cummins). A particularly common method in the industry to increase milk production is the injection of BST (a hormone), which has been shown to increase milk production in lactating cows. However, there can be undesirable side-effects of using BST. Another approach to increasing milk production is the use of monensin sodium (CAS REG. # 22373-78-0) sold under the tradename RUMENSIN®. However, administration of RUMENSIN® must be tightly controlled because overdosing can be detrimental to health and milk production.

Yucca extract and yucca powers have been used as feed additives for beef, swine, and poultry applications. However, Yucca extract was found to not increase milk production in dairy cows when fed as a portion of their daily feed. Wilson et al., 1998, *J. Dairy Sci.*, 81:1022-1027.

Accordingly, a need exists for methods and compositions that will increase milk production in animals.

SUMMARY OF THE INVENTION

The invention is related to methods and compositions for increasing milk production in animals using a Yucca drench product. In an embodiment, the invention is a method for increasing milk production of an animal comprising administering an initiation dose of a saponin-containing composition to the animal within five days before or after the time of freshening of the animal, and administering a plurality of maintenance doses of the saponin-containing composition to the animal.

The above summary of the present invention is not intended to describe each discussed embodiment of the present invention. This is the purpose of the detailed description that follows.

DETAILED DESCRIPTION OF THE INVENTION

Figure 1:
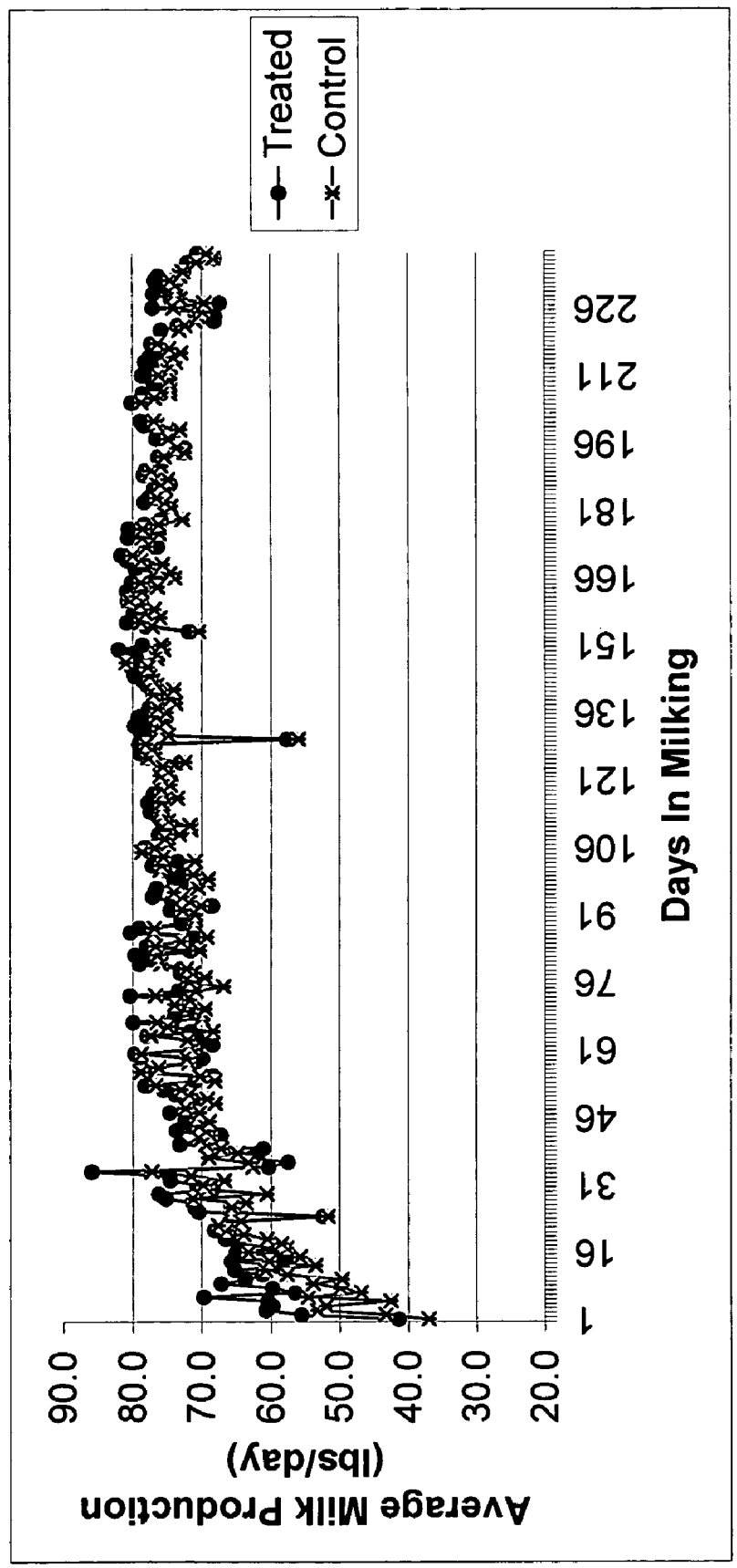
FIG. 1 is a graph showing average daily milk production over time for a test group of dairy cattle and a control group of dairy cattle.

It has been surprisingly found that a dose of a saponin containing composition, such as a Yucca extract, given to dairy cows at the time they freshen (give birth), followed by an amount in their daily ration, significantly improves milk production. In an embodiment, the invention is a method for increasing milk production of an animal comprising administering an initiation dose of a saponin-containing composition to the animal within five days before or after the time of freshening of the animal, and administering a plurality of maintenance doses of the saponin-containing composition to the animal.

Yucca extract has been fed to beef cattle as a flavor in the past. The Yucca plant has been grazed by beef cattle and is sought out as a food source, especially the flowers of the plant. Yucca extract, as an additive to beef cattle finish rations, has been demonstrated to provide improved feed efficiency and weight gain when compared to untreated controls. The inclusion of Yucca extract in the ration beef cattle as a grain-tempering agent improved feed efficiency and weight gain as well as increased moisture uptake of feed grain prior to processing. Zinn et al., 1998, *J. Anim. Sci.*, 76: 2239-2246.

However, when Yucca extract was fed to dairy cows as a portion of their daily feed, it was found to not increase milk production. Wilson et al., 1998, *J. Dairy Sci.*, 81:1022-1027. This study used a relatively small amount of yucca extract included in the diet on a daily basis and did not yield an increase in milk production. Therefore, it was surprising when it was discovered than an increase in milk production can result from the use of a yucca-extract based drench product. Specifically, it was unexpected that an increased dose of Yucca extract given to dairy cows at the time they freshen (give birth), followed by a small amount included in their daily ration, would significantly improve milk production. It is believed that the Wilson study on increasing milk production using yucca extract was ineffective because a large enough dose was not given at the correct time in the cow's lactation cycle. As shown in the examples below, new data is provided showing that a larger dose of saponins in the form of a yucca extract or powder followed by a lower maintenance dose increases milk production in lactating cows.

It is known that some bacteria (termed methanogens) living in the rumen of the dairy cow produce methane. Rumen protozoa have been shown to produce hydrogen in the rumen, which is then utilized by the methanogens to produce methane, which is then belched out of the cow during eructation. Methane production is carried on at the nutrient-expense of the host cow.

It is believed that the increased milk production resulting from the methods described herein is in-part due to increased amounts of available nutrients resulting from a reduction in the population of methane producing bacteria that are attached to protozoa in the rumen (or fore stomach) of the dairy cow. As methane is a green house gas, reducing the amount of methane produced by dairy cows and/or other domesticated ruminants could also reduce the impact that farming has on global warming. This is because according to some estimates, 17% of the methane in the atmosphere is attributable to livestock production.

Saponins can play a role in reducing or eliminating rumen protozoa, as shown in Examples 2 and 3 below. Saponins (triterpenoid, steroidal, or alkaloid) have a haemolytic action that is believed to be related to their affinity for cell membrane sterols that are embedded in the lipid bi-layer, particularly cholesterol. Saponins have been shown to form insoluble complexes with cholesterol and thereby open holes in cell membranes. The ability of saponins to rupture cell membranes, but yet be non-toxic to mammals when ingested orally makes them a suitable protozoan eliminator for use in livestock.

The addition of a large amount of saponin containing *Yucca* extract at the time of freshening, to reduce protozoa, followed by a reduced level of *Yucca* extract in the feed unexpectedly significantly increased milk production. Further, high dose oral administration of *Yucca* extract has caused no observed ill effects on the health of dairy cows.

Saponin-Containing Compositions:

Saponin-containing *Yucca* compositions in accordance with the invention may not be effective if they do not contain a sufficient amount of saponins. In an embodiment, the saponin containing composition used in accordance with the invention comprises at least 0.1% by weight saponins as measured by HPLC. In an embodiment, the saponin containing composition used in accordance with the invention comprises at least 0.5% by weight saponins as measured by HPLC. In a particular embodiment, the saponin containing composition used in accordance with the invention comprises at least 1.0% by weight saponins as measured by HPLC. It is believed that the effects of the composition are related to the total amount of saponins present. Thus, one of skill in the art will appreciate that if a certain amount of saponins is desired it can be achieved either through varying the volume of a certain concentration composition administered, varying the concentration of a certain volume of a composition, or both.

As different plant types contain varying concentrations of saponins, only extracts from some types of plants may be effective in accordance with the invention. By way of example, saponins useful in the present invention may also be extracted in sufficient concentrations from plants of the family: Amaryllidaccae, genus: *Agave*, which grows extensively in the southwestern United States and in Mexico. Saponins useful in the present invention may also be extracted in sufficient concentrations from plants of the family: Lillaecae, genus: *Yucca*, as well as from *Quillaja saponaria* bark. Saponins useful in the present invention may also be extracted from fenugreek, tea, soybeans, peas, yams, or sugar beets. Saponins may be extracted from plant materials in accordance with techniques well-known by those of skill in the art.

Exemplary liquid solutions containing saponins are available commercially and sold under the trademarks SAR-TEMP®, SARSTART®, SARSTART® PRO, and SARSTART® PLUS by SarTec Corporation of Anoka, Minn. These solutions are prepared by blending an aqueous extract of the plants of the family: Lillaecae, genus: *Yucca*, or other appropriate *Yucca* plants with antifreeze agents such as calcium chloride, propylene glycol, and the like, to depress the freezing point to approximately −30° F. These liquid solutions may also comprise a variety of other components. By way of example, SARSTART® PLUS can contain the following ingredients: Water, Propylene Glycol, *Yucca Shidegera* Extract, Vitamin E (as di-alpha-tocopheryl acetate), Vitamin A Propionate, Vitamin A Palmitate, Vitamin B1, Vitamin B2, Vitamin B6, Vitamin B12, D-Activated Animal Sterol (source of Vitamin D3), Naturally Occurring Organisms, Dried Egg Solids, Dried Casein, and Dried Whey. The physical and chemical characteristics of SARSTART® PLUS are as follows: Boiling Point: 240 F; Specific Gravity: 1; Melting Point: −20 F; Solubility in Water: Miscible; Appearance and Odor: Dark brown liquid with a mild odor and a slightly acid taste. Saponin containing compositions can also be formulated as dry powder. Such dry formulations are available commercially (SARSTART® D, SARSTART® DSC, SarTec Corporation, Anoka, Minn.). Dry powder formulations of saponin containing compositions may be added to the feed ration via a micro-ingredient machine or added to a feed mix truck and mixed thoroughly to assure even distribution in the feed.

Saponin containing compositions can be administered through many different means known to those of skill in the art. For example, liquid saponin containing compositions can be administered orally through the use of a drench gun.

The typical saponin content that naturally occurs in *yucca* plants is from 0.1-2% saponins by weight. *Yucca* extracts can be derived by extracting *yucca* powder with an aqueous solution that may or may not contain some fraction of organic solvent such as methanol, ethanol, propanol, butanol, or the like. Commercially available *Yucca* extracts can have a total solids content usually in the range from 5-50%. The saponin content of a typical 50 brix (50% solids by weight) *yucca* extract is usually in the range of about 1-2% saponins by weight as measured by HPLC analysis. Another method of measuring total saponin content is the extraction of all soluble components into a butanol extract followed by gravimetric analysis of the compounds dissolved in the butanol fraction. Measuring saponin content by the butanol extract method typically results in higher numbers than the more advanced HPLC method. Accordingly, the typical 50 brix (50% solids by weight) *yucca* extract is usually in the range of about 5-20.0% saponins content by weight as measured by the butanol extract method.

Dosing of *Yucca* Compositions:

*Yucca* containing compositions in accordance with the invention may be in liquid or dry forms. By way of example, a *yucca* containing plant extract may be dried into a powder form. In this form, the *yucca* containing composition may be administered to an animal as a pill or bolus, or mixed in with other components such as a feed ration. *Yucca* containing plant extract may also be in a solution with an amount of a carrier liquid such as water. In this form, the *yucca* containing composition may be administered to an animal as a liquid drench.

*Yucca* containing compositions may be administered to an animal as a single larger dose, at or around the time of freshening, followed by a smaller daily dose thereafter. The smaller daily dose may be continued through the milking cycle. In an embodiment, the smaller daily dose is continued for at least 30 days. In an embodiment, the smaller daily dose is continued for at least 60 days.

In an embodiment of the invention, the initiation dose is larger than each of the maintenance doses. In an embodiment the initiation dose is at least 10 times larger than the daily dose. In an embodiment, the initiation dose is at least 25 times larger than the daily dose. In a particular embodiment, the initiation dose is at least 50 times larger than the daily dose.

In some embodiments, the initiation dose comprises at least about 50 ml of a composition containing at least about 0.1 wt. % saponins as measured by HPLC analysis. In some embodiments, the initiation dose comprises at least about 100 ml of a composition containing at least about 0.1 wt. % saponins as measured by HPLC analysis. In some embodiments, the initiation dose comprises at least about 150 ml of a composition containing at least about 0.1 wt. % saponins as measured by HPLC analysis. In some embodiments, the initiation dose comprises at least about 200 ml of a composition containing at least about 0.1 wt. % saponins as measured by HPLC analysis. In some embodiments, the initiation dose comprises at least about 250 ml of a composition containing at least about 0.1 wt. % saponins as measured by HPLC analysis.

Cows that have previously been through a lactation cycle (lactation 2, 3, 4, etc. cows) are typically larger and have a larger rumen than those of the same type that have not been through a lactation cycle (lactation 1 cows). In an embodiment, cows that have previously been through a lactation cycle are given a larger initiation dose than lactation 1 cows.

The initiation dose is administered at, or around, the time of freshening. For example, in an embodiment, the initiation dose is administered within five days before or after the time of freshening (calving). In some applications, the initiation dose may need to be administered close to the time of freshening. In an embodiment, the initiation dose is administered within 48 hours before or after the time of freshening. The initiation dose may also be administered within 24 hours before or after the time of freshening. In a specific embodiment, the initiation dose is administered the same day as freshening.

Co-Agents:

One of skill in the art will appreciate that saponin-containing compositions may be administered to animals alone or in combination with other agents, such as anti-microbial co-agents, vitamins, feed stocks, etc. By way of example, a *yucca* containing composition may be administered with an agent containing a chlorate group (salts of chloric acid), such as sodium chlorate, potassium chlorate, and the like. Other anti-microbial agents that can be administered in combination with a *yucca* containing composition include antibiotics (such as neomycin and the like), and other chlorine containing compounds.

The combination of a methane inhibitor such as mevastatin or lovastatin, and a defaunating agent, such as *Yucca* extract, administered after calving may increase milk production even more than just the administration of a saponin-containing composition alone. In an embodiment, the invention comprises administering a saponin-containing composition along with a methane inhibitor.

The present invention may be better understood with reference to the following examples. These examples are intended to be representative of specific embodiments of the invention, and are not intended as limiting the scope of the invention.

EXAMPLES

Example 1

Increased Milk Production in Response to *Yucca* Extract

Adult, female dairy Holsteins were randomly assigned to either a treatment group or a control group in numbers show below in Table 1. Both groups of animals were managed, housed, fed and watered in accordance with standard commercial procedures. Both groups were being treated with BST. A 50 ml dose of a liquid composition (SARSTART® PLUS, SarTec, Anoka, Minn.) containing about 0.1 wt. % (HPLC) saponins was given via oral drench within 24 hours of the time of freshening (calving time) to treatment group cows freshening within the first 60 days of the study, these cows were then given a 2 ml daily dose of a composition (SARSTART® LSC, SarTec, Anoka, Minn.) also containing about 0.1 wt. % saponins (per head per day) added to the total mixed ration up until day 60 of the study and thereafter given a 4 ml daily dose of a composition (SARSTART® LSC, SarTec, Anoka, Minn.) containing about 0.1 wt. % saponins (per head per day) added to the total mixed ration for the remaining duration of the study. Treatment group cows freshening after the first 60 days of the study were given a 75 ml initiation dose of a liquid composition (SARSTART® LSC, SarTec, Anoka, Minn.) containing about 0.1 wt. % saponins followed by 4 ml daily dose of a composition (SARSTART® LSC, SarTec, Anoka, Minn.) containing about 0.1 wt. % saponins (per head per day) added to the total mixed ration for the remaining duration of the study. The total pounds of milk produced by each cow was recorded each day (except for days 7, 146, 153-154, 173, 175, 181-182, 186, 193, 197, 199, 203-205, 220-221, and 236 and the average for both the treated cows and the control cows was calculated. The data are shown in Table 1 below and in FIG. 1.

TABLE 1

Milk Production Study

| Day | Treatment Avg. | Control Avg. | # of Cows on Treatment | # of Control Cows |
|---|---|---|---|---|
| 1 | 41.4 | 37.0 | 9 | 11 |
| 2 | 55.5 | 43.3 | 14 | 11 |
| 3 | 60.7 | 53.3 | 14 | 11 |
| 4 | 59.8 | 52.0 | 14 | 12 |
| 5 | 60.4 | 42.6 | 18 | 24 |
| 6 | 69.6 | 54.5 | 23 | 27 |
| 7 | | | | |
| 8 | 56.5 | 46.9 | 28 | 35 |
| 9 | 59.8 | 49.9 | 27 | 34 |
| 10 | 67.1 | 53.8 | 33 | 41 |
| 11 | 63.7 | 49.7 | 34 | 42 |
| 12 | 61.2 | 57.7 | 34 | 42 |
| 13 | 65.2 | 60.8 | 39 | 46 |
| 14 | 58.4 | 53.5 | 37 | 47 |
| 15 | 65.7 | 60.3 | 38 | 47 |
| 16 | 56.6 | 55.7 | 44 | 51 |
| 17 | 65.0 | 63.3 | 48 | 52 |
| 18 | 59.7 | 57.7 | 48 | 52 |
| 19 | 64.7 | 58.5 | 48 | 51 |
| 20 | 66.5 | 60.6 | 51 | 52 |
| 21 | 64.3 | 63.9 | 53 | 56 |
| 22 | 68.1 | 66.4 | 53 | 57 |
| 23 | 66.8 | 67.6 | 53 | 57 |
| 24 | 65.9 | 64.4 | 54 | 62 |
| 25 | 52.4 | 51.7 | 54 | 62 |
| 26 | 70.4 | 65.8 | 51 | 62 |
| 27 | 70.9 | 65.7 | 58 | 70 |
| 28 | 71.1 | 63.7 | 60 | 71 |
| 29 | 75.1 | 71.3 | 60 | 72 |
| 30 | 76.2 | 60.6 | 61 | 75 |
| 31 | 68.4 | 69.2 | 67 | 77 |
| 32 | 70.7 | 69.8 | 67 | 78 |
| 33 | 74.5 | 66.7 | 67 | 78 |
| 34 | 74.7 | 71.5 | 71 | 89 |
| 35 | 85.9 | 77.2 | 73 | 90 |
| 36 | 60.4 | 62.7 | 76 | 92 |
| 37 | 57.5 | 63.3 | 76 | 92 |
| 38 | 62.8 | 69.0 | 76 | 92 |
| 39 | 61.9 | 64.8 | 76 | 92 |

TABLE 1-continued

Milk Production Study

| Day | Treatment Avg. | Control Avg. | # of Cows on Treatment | # of Control Cows |
|---|---|---|---|---|
| 40 | 61.1 | 67.2 | 76 | 91 |
| 41 | 73.1 | 69.4 | 92 | 104 |
| 42 | 70.0 | 70.2 | 95 | 109 |
| 43 | 67.2 | 68.7 | 95 | 110 |
| 44 | 73.6 | 69.4 | 99 | 119 |
| 45 | 71.3 | 70.3 | 102 | 120 |
| 46 | 72.4 | 68.9 | 102 | 120 |
| 47 | 71.2 | 70.7 | 102 | 119 |
| 48 | 74.6 | 70.3 | 107 | 127 |
| 49 | 72.4 | 72.3 | 109 | 131 |
| 50 | 71.2 | 68.0 | 109 | 133 |
| 51 | 71.3 | 69.2 | 112 | 145 |
| 52 | 73.8 | 71.8 | 114 | 147 |
| 53 | 75.5 | 72.9 | 114 | 147 |
| 54 | 78.2 | 76.6 | 114 | 147 |
| 55 | 70.9 | 68.1 | 122 | 155 |
| 56 | 68.3 | 70.2 | 124 | 158 |
| 57 | 78.0 | 78.8 | 124 | 157 |
| 58 | 78.8 | 76.2 | 127 | 162 |
| 59 | 70.9 | 71.8 | 129 | 163 |
| 60 | 69.9 | 72.1 | 129 | 163 |
| 61 | 79.6 | 78.7 | 129 | 163 |
| 62 | 70.9 | 71.3 | 133 | 165 |
| 63 | 68.4 | 71.8 | 137 | 170 |
| 64 | 70.5 | 72.0 | 137 | 170 |
| 65 | 77.8 | 77.3 | 139 | 175 |
| 66 | 71.5 | 68.3 | 142 | 178 |
| 67 | 74.3 | 74.9 | 142 | 178 |
| 68 | 79.9 | 76.4 | 141 | 178 |
| 69 | 73.9 | 69.9 | 150 | 185 |
| 70 | 70.8 | 69.8 | 150 | 185 |
| 71 | 73.6 | 69.5 | 150 | 184 |
| 72 | 73.2 | 73.9 | 158 | 187 |
| 73 | 73.6 | 71.6 | 163 | 189 |
| 74 | 80.4 | 76.7 | 163 | 189 |
| 75 | 73.3 | 70.8 | 162 | 187 |
| 76 | 72.0 | 66.8 | 170 | 192 |
| 77 | 71.2 | 71.8 | 170 | 192 |
| 78 | 70.7 | 69.5 | 173 | 195 |
| 79 | 73.0 | 71.2 | 173 | 195 |
| 80 | 72.9 | 72.2 | 180 | 199 |
| 81 | 79.0 | 75.9 | 180 | 199 |
| 82 | 77.5 | 76.3 | 179 | 199 |
| 83 | 79.7 | 76.4 | 178 | 198 |
| 84 | 71.7 | 70.3 | 183 | 213 |
| 85 | 78.0 | 76.6 | 183 | 213 |
| 86 | 72.6 | 73.0 | 183 | 211 |
| 87 | 71.1 | 69.2 | 195 | 215 |
| 88 | 80.3 | 77.0 | 195 | 214 |
| 89 | 79.0 | 76.9 | 194 | 214 |
| 90 | 72.8 | 71.1 | 198 | 221 |
| 91 | 72.9 | 70.9 | 198 | 223 |
| 92 | 72.9 | 70.9 | 198 | 223 |
| 93 | 74.5 | 72.7 | 198 | 227 |
| 94 | 68.5 | 70.1 | 199 | 228 |
| 95 | 74.3 | 71.6 | 200 | 227 |
| 96 | 77.1 | 72.7 | 199 | 228 |
| 97 | 76.8 | 74.0 | 199 | 227 |
| 98 | 76.5 | 70.5 | 204 | 239 |
| 99 | 72.9 | 69.3 | 204 | 241 |
| 100 | 74.0 | 69.0 | 204 | 241 |
| 101 | 72.8 | 71.1 | 207 | 240 |
| 102 | 75.4 | 76.0 | 206 | 240 |
| 103 | 77.1 | 75.8 | 206 | 240 |
| 104 | 73.4 | 70.9 | 210 | 247 |
| 105 | 76.0 | 75.5 | 216 | 248 |
| 106 | 76.7 | 78.7 | 215 | 248 |
| 107 | 78.2 | 76.8 | 222 | 256 |
| 108 | 76.3 | 74.8 | 224 | 257 |
| 109 | 75.9 | 75.3 | 224 | 257 |
| 110 | 76.2 | 73.2 | 223 | 255 |
| 111 | 73.1 | 71.5 | 239 | 267 |
| 112 | 74.3 | 71.7 | 237 | 266 |
| 113 | 75.8 | 74.8 | 237 | 266 |
| 114 | 76.3 | 75.6 | 240 | 275 |
| 115 | 77.4 | 75.9 | 246 | 274 |
| 116 | 77.4 | 75.7 | 246 | 274 |
| 117 | 77.8 | 75.8 | 245 | 273 |
| 118 | 75.4 | 73.5 | 251 | 275 |
| 119 | 76.9 | 75.6 | 253 | 275 |
| 120 | 75.3 | 75.8 | 253 | 275 |
| 121 | 75.0 | 74.5 | 253 | 274 |
| 122 | 74.5 | 75.7 | 253 | 274 |
| 123 | 75.8 | 76.0 | 252 | 274 |
| 124 | 75.2 | 74.9 | 263 | 280 |
| 125 | 75.3 | 75.6 | 262 | 280 |
| 126 | 73.0 | 72.3 | 261 | 277 |
| 127 | 77.8 | 77.8 | 259 | 277 |
| 128 | 78.9 | 76.8 | 258 | 276 |
| 129 | 78.2 | 77.2 | 261 | 281 |
| 130 | 79.0 | 78.1 | 261 | 281 |
| 131 | 57.6 | 56.0 | 260 | 281 |
| 132 | 78.7 | 74.8 | 262 | 289 |
| 133 | 78.3 | 76.1 | 266 | 290 |
| 134 | 79.7 | 76.1 | 270 | 298 |
| 135 | 78.0 | 75.2 | 269 | 298 |
| 136 | 79.1 | 76.5 | 278 | 302 |
| 137 | 76.1 | 75.1 | 278 | 302 |
| 138 | 77.6 | 76.4 | 278 | 300 |
| 139 | 76.2 | 73.7 | 289 | 308 |
| 140 | 75.9 | 74.5 | 288 | 308 |
| 141 | 77.0 | 77.0 | 299 | 311 |
| 142 | 77.1 | 74.0 | 305 | 315 |
| 143 | 77.8 | 76.5 | 301 | 314 |
| 144 | 78.5 | 77.0 | 304 | 316 |
| 145 | 79.7 | 77.5 | 304 | 316 |
| 146 | | | | |
| 147 | 80.2 | 77.8 | 310 | 320 |
| 148 | 79.9 | 81.0 | 312 | 327 |
| 149 | 79.4 | 76.5 | 312 | 327 |
| 150 | 79.9 | 76.3 | 317 | 331 |
| 151 | 82.0 | 75.5 | 317 | 331 |
| 152 | 78.5 | 75.8 | 317 | 331 |
| 153 | | | | |
| 154 | | | | |
| 155 | 71.8 | 70.4 | 329 | 340 |
| 156 | 78.0 | 77.1 | 328 | 340 |
| 157 | 80.9 | 78.8 | 336 | 345 |
| 158 | 78.6 | 76.0 | 336 | 345 |
| 159 | 79.9 | 78.1 | 336 | 345 |
| 160 | 78.2 | 76.8 | 341 | 346 |
| 161 | 78.7 | 78.9 | 341 | 346 |
| 162 | 80.7 | 80.5 | 341 | 346 |
| 163 | 80.6 | 79.4 | 341 | 346 |
| 164 | 80.9 | 78.6 | 352 | 357 |
| 165 | 79.5 | 76.4 | 352 | 357 |
| 166 | 80.1 | 78.8 | 352 | 357 |
| 167 | 76.6 | 73.8 | 352 | 357 |
| 168 | 75.8 | 74.6 | 357 | 367 |
| 169 | 79.6 | 76.1 | 360 | 369 |
| 170 | 78.2 | 75.6 | 361 | 368 |
| 171 | 80.9 | 78.7 | 365 | 369 |
| 172 | 81.7 | 80.0 | 365 | 369 |
| 173 | | | | |
| 174 | 76.3 | 78.0 | 374 | 375 |
| 175 | | | | |
| 176 | 80.6 | 78.6 | 378 | 375 |
| 177 | 77.5 | 76.1 | 385 | 379 |
| 178 | 80.5 | 78.5 | 395 | 385 |
| 179 | 78.2 | 76.2 | 394 | 385 |
| 180 | 75.8 | 72.7 | 394 | 385 |
| 181 | | | | |
| 182 | | | | |
| 183 | 74.9 | 74.4 | 395 | 389 |
| 184 | 78.3 | 75.3 | 395 | 388 |
| 185 | 77.6 | 76.5 | 400 | 392 |
| 186 | | | | |
| 187 | 76.9 | 75.1 | 399 | 391 |

TABLE 1-continued

Milk Production Study

| Day | Treatment Avg. | Control Avg. | # of Cows on Treatment | # of Control Cows |
|---|---|---|---|---|
| 188 | 74.5 | 75.9 | 406 | 394 |
| 189 | 76.6 | 74.9 | 406 | 393 |
| 190 | 78.3 | 77.7 | 406 | 393 |
| 191 | 78.1 | 77.2 | 416 | 407 |
| 192 | 75.9 | 75.9 | 416 | 407 |
| 193 | | | | |
| 194 | 76.2 | 75.3 | 412 | 404 |
| 195 | 72.5 | 72.4 | 429 | 426 |
| 196 | 72.4 | 73.5 | 429 | 426 |
| 197 | | | | |
| 198 | 76.5 | 74.8 | 434 | 431 |
| 199 | | | | |
| 200 | 73.4 | 73.1 | 433 | 431 |
| 201 | 78.3 | 76.4 | 433 | 430 |
| 202 | 78.8 | 76.8 | 443 | 434 |
| 203 | | | | |
| 204 | | | | |
| 205 | | | | |
| 206 | 80.1 | 78.7 | 446 | 442 |
| 207 | 78.0 | 76.8 | 446 | 442 |
| 208 | 78.5 | 74.5 | 446 | 442 |
| 209 | 76.8 | 74.5 | 446 | 447 |
| 210 | 75.6 | 74.5 | 441 | 447 |
| 211 | 77.0 | 74.6 | 441 | 453 |
| 212 | 78.6 | 76.1 | 441 | 453 |
| 213 | 77.4 | 74.7 | 441 | 453 |
| 214 | 77.1 | 74.4 | 441 | 453 |
| 215 | 78.1 | 73.7 | 434 | 453 |
| 216 | 77.5 | 74.0 | 433 | 463 |
| 217 | 76.3 | 72.9 | 433 | 463 |
| 218 | 76.9 | 74.6 | 436 | 466 |
| 219 | 77.2 | 76.3 | 435 | 457 |
| 220 | | | | |
| 221 | | | | |
| 222 | 75.8 | 73.1 | 434 | 457 |
| 223 | 73.3 | 72.3 | 436 | 461 |
| 224 | 68.1 | 70.8 | 444 | 466 |
| 225 | 68.0 | 70.4 | 444 | 466 |
| 226 | 70.2 | 69.8 | 443 | 464 |
| 227 | 77.0 | 74.0 | 447 | 472 |
| 228 | 67.4 | 69.6 | 447 | 472 |
| 229 | 74.4 | 73.0 | 446 | 470 |
| 230 | 76.9 | 73.8 | 455 | 474 |
| 231 | 74.6 | 73.7 | 455 | 472 |
| 232 | 75.5 | 73.7 | 454 | 474 |
| 233 | 76.7 | 74.5 | 453 | 473 |
| 234 | 76.2 | 73.1 | 454 | 473 |
| 235 | 72.5 | 72.6 | 454 | 473 |
| 236 | | | | |
| 237 | 72.0 | 70.7 | 462 | 485 |
| 238 | 68.1 | 68.3 | 467 | 488 |
| AVG. | 73.7 | 71.6 | | |

The data show that treated animals produced an average of 2.1 pounds of milk per day more than control animals over the course of the study.

Example 2

Effects of a Saponin Containing Extract on Protozoal Counts in Cattle

Four crossbred yearling cattle were selected as subjects. The cattle weighed an average of 725 lbs at the time of surgery. Rumen fistulas were installed and 4" cannulas were utilized to seal the fistula. The cattle were maintained on a forage ration for the duration of the study. The ration (grass hay; 10.5% CP, 55% NDF) was fed for ad libitum access.

The preliminary phase involved establishment of baseline protozoal numbers. On day 0, rumen evacuations were done on each steer to estimate rumen volume. Following evacuation, samples were taken on each of seven consecutive days to determine day-to-day variation. Samples were collected each day between 0800 and 0900 hours and processed according to the methods of Dehority, 1984, *Appl. Environ. Micro.*, 48:182-185. Data for the preliminary phase are shown in Table 2 below.

TABLE 2

Preliminary Phase (baseline)

| Steer # | Volume (L) | Protozoal Counts ($10^4$/ml) | Total Protozoa ($\times 10^9$) |
|---|---|---|---|
| 1 | 61.4 | 35.5 ± 6.4 | 21.8 |
| 2 | 54.4 | 26.9 ± 6.9 | 14.6 |
| 3 | 50.9 | 49.2 ± 6.5 | 25.0 |
| 4 | 46.8 | 44.4 ± 5.0 | 20.8 |
| mean | 53.4 | 39.0 ± 6.2 | 20.6 |

The experimental phase involved dosing the cattle with a saponin-containing composition, containing about 0.1% Saponins, to test the hypothesis that the product exhibits anti-protozoal activity. Two steers were chosen randomly (#1 and #4) to receive the experimental treatment, which consisted of 50 ml of the saponin-containing composition. The two remaining steers (#2 and #3) received a control treatment, which consisted of 50 ml of isotonic saline. Steers were dosed at 0700 hours on a Monday and sampled at 12, 24, 48, 72, 96, and 108 hours later. Data for the experimental phase are shown in Table 3 below.

TABLE 3

Treatment Phase

| Steer # | Mean Baseline Count ($\times 10^4$) | Mean Baseline Total Protozoa ($\times 10^9$) | Mean Treated Count ($\times 10^4$) | Mean Treated Total Protozoa ($\times 10^9$) | % Change in Counts | % Change in Total |
|---|---|---|---|---|---|---|
| 1 | 35.5 | 21.8 | 31.5 | 19.3 | −11.3 | −11.5 |
| 2 | 26.9 | 14.6 | 27.3 | 14.9 | +1.0 | +2.0 |
| 3 | 49.2 | 25.0 | 50.4 | 25.7 | +1.0 | +2.8 |
| 4 | 44.4 | 20.8 | 38.3 | 17.9 | −13.7 | −14.0 |

The data show that administration of a saponin containing composition resulted in an 11.5-14% reduction in protozoal counts in the rumen in vivo.

Example 3

Effects of a Saponin Containing Extract at Increased Concentration on Protozoal Counts in Cattle Two crossbred yearling cattle were used for this study. The ration (grass hay; 10.5% CP, 55% NDF) was fed for ad libitum access. The preliminary phase involved establishment of baseline protozoal numbers. On day −2, rumen evacuations were done on each steer to estimate rumen volume. Following evacuation, samples were taken on two consecutive days (days −2 and −1) to determine day-to-day variation. Samples were collected each day between 0800 and 0900 hours and processed according to the methods of Dehority, 1984, *Appl. Environ. Micro.*, 48:182-185. Data for the preliminary phase are shown in Table 4.

TABLE 4

Preliminary Phase (baseline)

| Steer # | Volume (L) | Protozoal Counts ($10^4$/ml) | Total Protozoa ($10^{10}$) |
| --- | --- | --- | --- |
| 1 | 53.4 | 45.6 ± 7.1 | 2.4 |
| 2 | 56.0 | 53.1 ± 9.0 | 3.0 |
| mean | 54.7 | 49.4 ± 8.0 | 2.6 |

*average of two days

The experimental phase involved dosing the cattle with a saponin-containing composition (0.1% saponins by weight) to test the hypothesis that additional levels of the product display increasing levels of antiprotozoal activity. Steers were subjected to the following treatment and sampling protocol:

| | |
| --- | --- |
| Day 1 | 1 × Dose (50 ml) |
| Day 2 | Sampled for Protozoa |
| Day 5 | 2 × Dose (100 ml) |
| Day 6 | Sampled for Protozoa |
| Day 9 | 10 × Dose (500 ml) |
| Day 10 | Sampled for Protozoa |

Data for the treatment phase are shown below in Table 5.

TABLE 5

| | | Treatment Phase Counts ($10^4$/ml) | | | | | |
| --- | --- | --- | --- | --- | --- | --- | --- |
| Steer # | Baseline | 1× | (% decline) | 2× | (% decline) | 10× | (% decline) |
| 1 | 53.4 | 44.9 | (−15.9) | 40.6 | (−24.0) | 31.1 | (−41.8) |
| 2 | 56.0 | 48.2 | (−13.9) | 42.9 | (−23.4) | 34.2 | (−38.9) |
| Mean | 54.7 | 46.6 | (−14.9) | 41.8 | (−23.7) | 32.7 | (−40.3) |

The data in this example show that administration of a saponin containing composition in a dosage of 50 ml resulted in a 14.9% reduction in protozoal counts, administration of the same composition but in a dosage of 100 ml resulted in a 23.7% reduction in protozoal counts, and administration of the same composition at a dosage of 500 ml resulted in a 40.3% reduction in protozoal counts. The data show that the saponin containing composition can reduce protozoal counts in a dose-dependent fashion with larger doses resulting in greater reductions in the rumen of steers in vivo.

Example 4

Effects of a Saponin Containing Extract on Milk Production in Dairy Cattle

A total of 685 adult, female dairy Holsteins were randomly assigned to either a treatment group or a control group in numbers show below in Table 1. Both groups of animals were managed, housed, fed and watered in accordance with standard commercial procedures. Both groups were being treated with bovine somatotropin (BST) and for the first 30 days of the trial also received RUMENSIN® (Elanco, Greenfield, Ind.) in the diet. A 100 ml dose of a liquid composition (SARSTART® PLUS, SarTec, Anoka, Minn.) containing about 0.1 wt. % saponins (HPLC) was administered via oral drench within 24 hours of the time of freshening (calving time) followed by 4 ml daily dose of a composition (SARSTART® LSC, SarTec, Anoka, Minn.) also containing about 0.1 wt. % saponins (per head per day) added to the total mixed ration for the duration of the trial for each cow for the treatment group. The total pounds of milk produced by each cow was recorded each day and the average for both the treated cows group and the control cows group was calculated.

Figure 2:
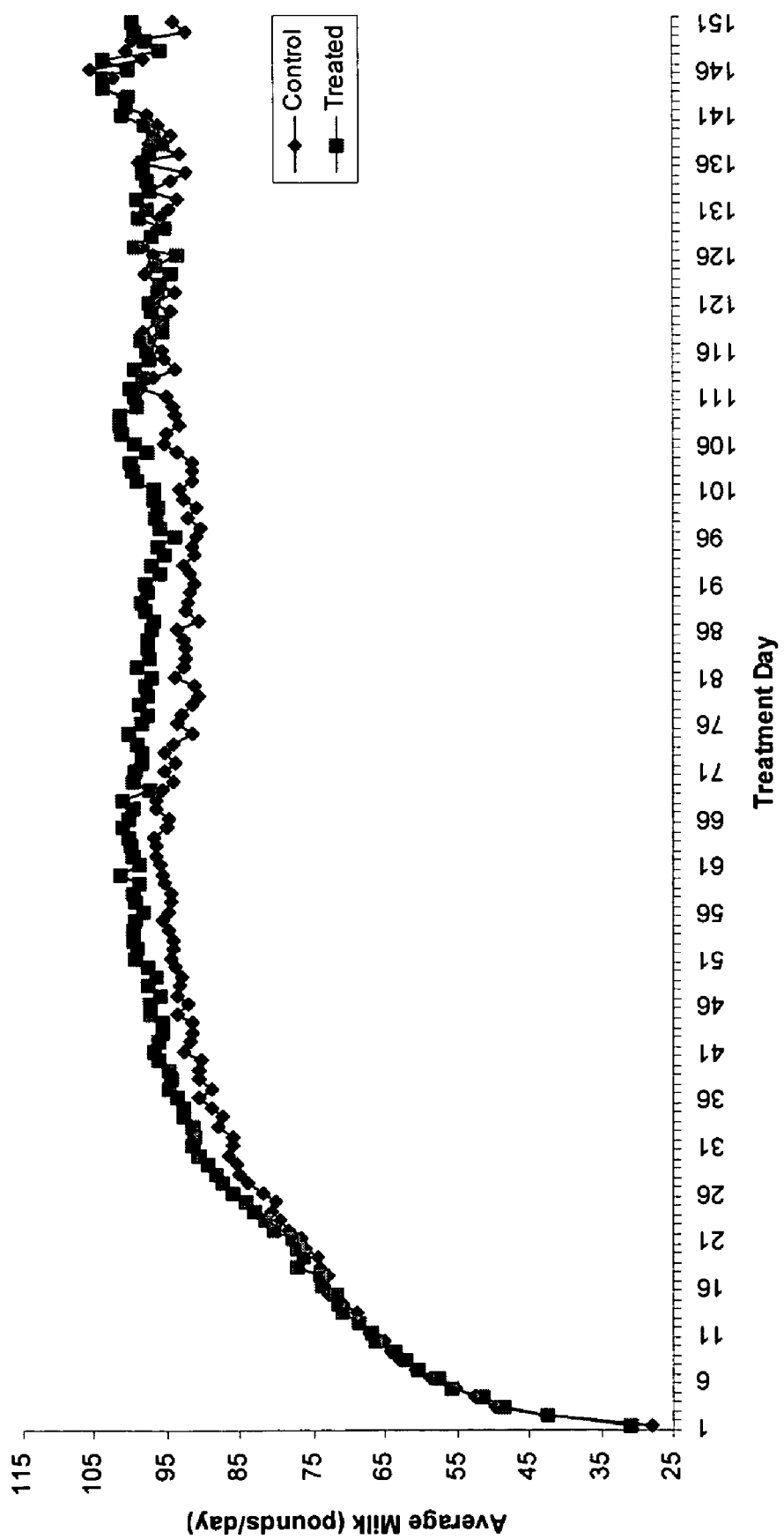
FIG. 2 is a graph showing average daily milk production over time for a test group of dairy cattle and a control group of dairy cattle in a different study.

As shown in FIG. 2, the treated cows produced an average of 4.4 lbs more milk per head per day than the control cows. This example shows that milk production can be enhanced by administration of a saponin containing composition even where the subject animals are already being treated with other milk-production enhancing agents (such as BST and RUMENSIN®).

Example 5

Effects of a Saponin Containing Extract on Milk Production in Dairy Cattle

A total of 404 adult, female dairy Holsteins were randomly assigned to either a treatment group or a control group in numbers show below in Table 1. Both groups were being treated with bovine somatotropin (BST) before and during the study. The study lasted a total of 180 days. Both groups of animals were managed, housed, fed and watered in accordance with standard commercial procedures. A 100 ml dose of a liquid composition (SARSTART PLUS, SarTec, Anoka, Minn.) containing about 0.1 wt. % saponins was given via oral drench within 24 hours of the time of freshening (calving time) to dairy cows followed by 4 ml daily dose of a composition (SARSTART LSC, SarTec, Anoka, Minn.) also containing about 0.1 wt. % saponins (per head per day) added to the total mixed ration for the duration of the trial for each cow for the treatment group. The total pounds of milk produced by each cow was recorded each day and the average for both the treated cows group and the control cows group was calculated.

Figure 3:
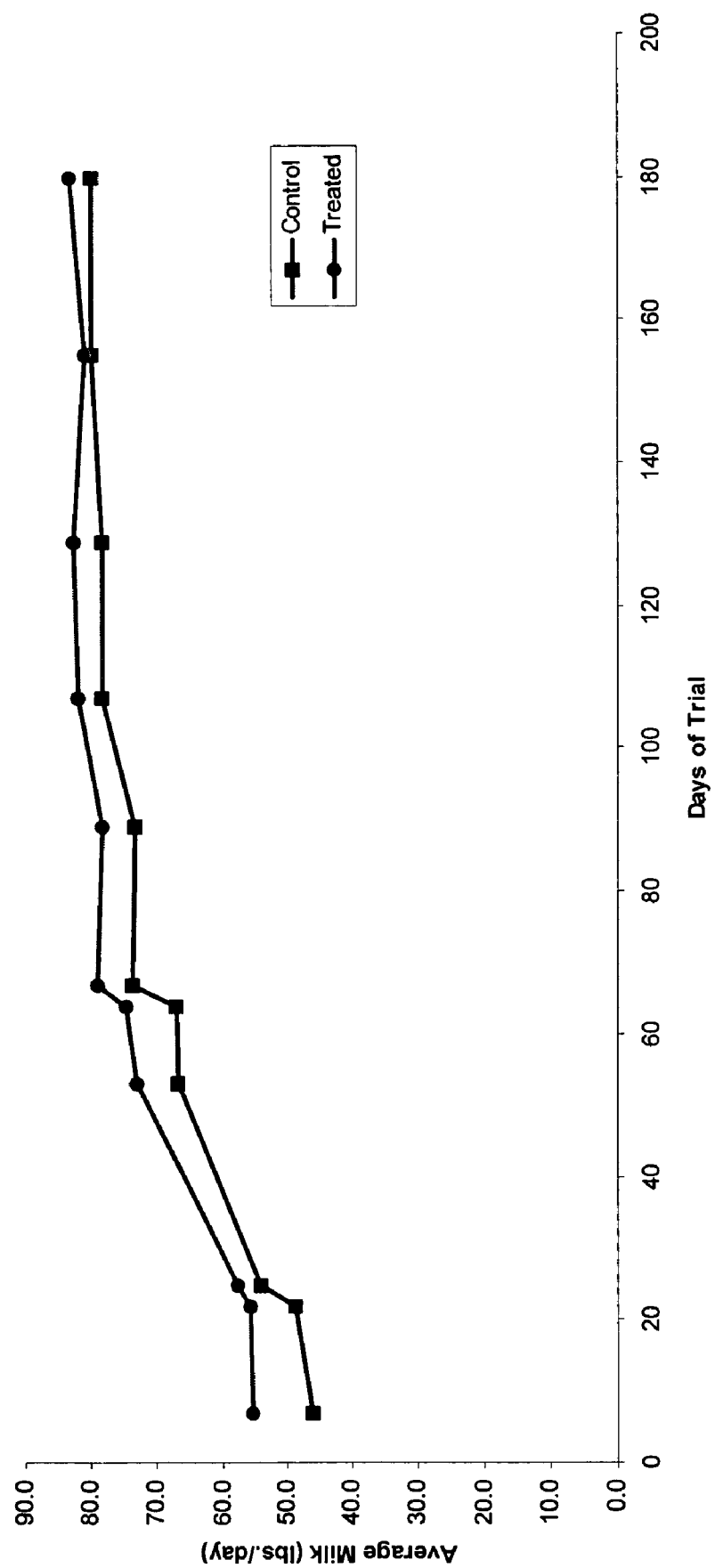
FIG. 3 is a graph showing average daily milk production over time for a test group of dairy cattle and a control group of dairy cattle in a different study.

The data are shown in FIG. 3. The data show that the treated cows produced an average of 5.1 lbs more milk per head per day than the control cows.

All references contained herein to amounts of saponins are as measured by HPLC analysis unless specifically indicated otherwise. All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

We claim:

1. A method for increasing the average pounds of milk produced per day of a dairy cow comprising:
   administering an initiation dose of a first composition comprising at least 0.1% by weight of saponins to the dairy cow within 24 hours before or after the time of freshening of the dairy cow, and
   administering a plurality of maintenance doses of a second composition comprising at least 0.1% by weight of saponins to the dairy cow;
   the initiation dose comprising a total amount of saponins at least ten times greater by weight than each of the maintenance doses,
   wherein saponins administered in the initiation dose and maintenance doses are provided in the form of a plant extract selected from the group consisting of *yucca* (*Yucca schidigera*), agave, quillaja, fenugreek, tea, soybeans, peas, yams, sugar beets, and mixtures thereof.

2. The method of claim 1, wherein the initiation dose contains a total amount of saponins at least twenty five times greater by weight than each of the maintenance doses.

3. The method of claim 1, wherein said plant extract comprises *yucca* (*Yucca schidigera*), agave, or quillaja extract.

4. The method of claim 1, wherein said plant extract comprises *yucca* (*Yucca schidigera*) extract.

5. The method of claim 1, the first composition comprising sarsaponins.

6. The method of claim 1, the second composition comprising sarsaponins.

7. The method of claim 1, wherein the first composition and the second composition are the same.

8. The method of claim 1, fun her comprising administration of a methane inhibitor.

* * * * *

UNITED STATES PATENT AND TRADEMARK OFFICE
CERTIFICATE OF CORRECTION

PATENT NO.         : 7,544,376 B2                                              Page 1 of 1
APPLICATION NO. : 11/193032
DATED              : June 9, 2009
INVENTOR(S)        : McNeff et al.

It is certified that error appears in the above-identified patent and that said Letters Patent is hereby corrected as shown below:

At Col. 14, line 19, claim 8:    "fun her comprising" should read --further comprising--

Signed and Sealed this

Twenty-first Day of July, 2009

JOHN DOLL
*Acting Director of the United States Patent and Trademark Office*